United States Patent
Oh et al.

(10) Patent No.: US 8,682,412 B2
(45) Date of Patent: Mar. 25, 2014

(54) TETRODE FOR MEASURING BIO-SIGNALS AND METHOD OF MANUFACTURING THE SAME

(75) Inventors: Se Jae Oh, Daegu (KR); Jei Won Cho, Ulwang-si (KR); Il Joo Cho, Seoul (KR); Soo Hyun Lee, Pohang-si (KR); Hee Sup Shin, Ulwang-si (KR); Jin Seok Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/409,862

(22) Filed: Mar. 1, 2012

(65) Prior Publication Data

US 2013/0131485 A1 May 23, 2013

(30) Foreign Application Priority Data

Nov. 23, 2011 (KR) ........................ 10-2011-0123070

(51) Int. Cl.
*A61B 5/04* (2006.01)
*A61N 1/00* (2006.01)

(52) U.S. Cl.
USPC ............ 600/378; 600/377; 600/544; 607/118

(58) Field of Classification Search
USPC ......... 600/372–373, 377–379, 393, 544–545; 607/115–118
See application file for complete search history.

(56) References Cited

U.S. PATENT DOCUMENTS

| | | | |
|---|---|---|---|
| 6,731,964 B2* | 5/2004 | Shenoy et al. | 600/372 |
| 6,978,183 B2* | 12/2005 | Rothman | 607/99 |
| 7,010,356 B2* | 3/2006 | Jog et al. | 607/116 |
| 7,107,104 B2* | 9/2006 | Keravel et al. | 607/116 |
| 7,774,053 B2* | 8/2010 | Garell et al. | 600/544 |
| 2003/0100823 A1* | 5/2003 | Kipke et al. | 600/378 |
| 2007/0060815 A1* | 3/2007 | Martin et al. | 600/372 |
| 2007/0123765 A1* | 5/2007 | Hetke et al. | 600/378 |
| 2008/0255439 A1* | 10/2008 | Tang et al. | 600/373 |
| 2010/0094382 A1* | 4/2010 | Pezaris et al. | 607/54 |

OTHER PUBLICATIONS

Korean Office Action mailed Mar. 15, 2013 for corresponding Korean Application No. 10-2011-0123070, pp. 1-7.
Jiayi Zhang et al., "Integrated device for optical stimulation and spatiotemporal electrical recording of neural activity in light-sensitized brain tissue", Journal of Neural Engineering, vol. 6, 2009, 055007, pp. 1-13.
Yi-Fang Liao et al., "A simple method for fabricating microwire tetrode with sufficient rigidity and integrity without a heat-fusing process", Journal of Neuroscience Methods, vol. 195, 2011, pp. 211-215.

(Continued)

*Primary Examiner* — Linda Dvorak
*Assistant Examiner* — Brian M Antiskay
(74) *Attorney, Agent, or Firm* — Staas & Halsey LLP

(57) ABSTRACT

A tetrode for measuring bio-signals, the tetrode including four electrodes which extend in a lengthwise direction of the tetrode and are symmertrically arranged; and an insulation layer which surrounds the four electrodes to insulate the electrodes from each others. A method of manufacturing a tetrode for measuring bio-signals, the method including forming a first insulation layer; forming first and second electrodes on the first insulation layer and forming a second insulation layer on the first and second electrodes; and forming third and fourth electrodes on the second insulation layer and forming a third insulation layer on the third and fourth electrodes.

13 Claims, 15 Drawing Sheets

(56) References Cited

OTHER PUBLICATIONS

André Mercanzini et al., "Demonstration of cortical recording using novel flexible polymer neural probes", Science Direct, Sensors and Actuators A, 2008, vol. 143, pp. 90-96.

S. Metz et al., "Flexible polyimide probes with microelectrodes and embedded mircrofluidic channels for simultaneous drug delivery and multi-channel monitoring of bioelectric activity", Biosensors and Bioelectronics, vol. 19, 2004, pp. 1309-1318.

* cited by examiner

TETRODE FOR MEASURING BIO-SIGNALS AND METHOD OF MANUFACTURING THE SAME

CROSS-REFERENCE TO RELATED PATENT APPLICATION

This application claims the benefit of Korean Patent Application No. 10-2011-0123070, filed on Nov. 23, 2011, in the Korean Intellectual Property Office, the disclosure of which is incorporated herein in its entirety by reference.

BACKGROUND OF THE INVENTION

1. Field of the Invention

The present invention relates to a tetrode for measuring bio-signals and a method of manufacturing the same, and more particularly, to a tetrode for measuring brain neural signals and a method of manufacturing the same.

2. Description of the Related Art

The human body includes a large number of neurons that function as information transmitting media. Exchange of information between neurons may be considered as being similar to transmission and reception of electrical signals. In other words, the neurons transmit information to other neurons by predetermined electrical signals, and thus, the neurons may be sensitive to external electrical stimulations.

Meanwhile, it is known that the human brain includes a large number of neurons. The brain neurons determine the brain functions and are categorized into various categories according to their functions. Therefore, to understand the brain functions, the functions and operations of the brain neurons have to be analyzed. For analysis of functions of brain neurons, methods including the analysis of electrical characteristics of brain neurons according to external stimulations and the analysis of body reactions according to electrical stimulations of particular brain neurons have been developed. A device used in experiments for determining the correlations between brain neurons and electrical signals, that is, a brain neuron single unit recording system, includes an electrode unit for detecting electrical signals of brain neurons or applying electrical signals to brain neurons, a micro-manipulator for moving the electrode unit close to the brain neurons, and a signal processing unit for converting electrical signals generated by the electrode unit to digital signals and analyzing the digital signals.

Since the brain is the most sensitive organ in the human body, the operation for applying electrical stimulation to the brain neurons or detecting electrical signals therefrom is very important. Therefore, researches are actively performed on electrode units for measuring electrical signals from the human body or applying electrical signals to the human body.

SUMMARY OF THE INVENTION

The present invention provides a tetrode for measuring bio-signals and a method of manufacturing the same.

According to an aspect of the present invention, there is provided a tetrode for measuring bio-signals, the tetrode including at least four electrodes which extend in a lengthwise direction of the tetrode and are apart from each others; and an insulation layer which insulates the electrodes from each others.

First end surfaces of the electrodes may be exposed to measure bio-signals.

End surfaces of the electrodes may have square shapes or circular shapes.

The electrodes may include four electrodes arranged in a square array shape.

At least one of the electrodes may apply electrical stimulation to a living body.

The tetrode may further include a channel between the electrodes, wherein a fluid may flow in the channel.

The tetrode may further include a light propagating tube arranged in the channel.

The tetrode may further include a reflective layer surrounding the light waveguide.

The insulation layer may contain a biocompatible polymer.

The insulation layer may contain a flexible polymer.

The insulation layer may contain polyimide or polydimethylsiloxane (PDMS).

The electrodes may contain conductive materials.

According to another aspect of the present invention, there is provided a tetrode array for measuring bio-signals, the tetrode array including a plurality of the tetrodes for measuring bio-signals, wherein the plurality of tetrodes for measuring bio-signals are arranged in a 2D array shape.

According to another aspect of the present invention, there is provided a method of manufacturing a tetrode for measuring bio-signals, the method including forming a first insulation layer; forming first and second electrodes on the first insulation layer and forming a second insulation layer on the first and second electrodes; and forming third and fourth electrodes on the second insulation layer and forming a third insulation layer on the third and fourth electrodes.

The step of forming the first insulation layer may include forming a sacrificing layer on a silicon wafer; and forming the first insulation layer on the sacrificing layer.

The method may further include forming a channel between the first and second electrodes on the second insulation layer; and forming a fourth insulation layer on the channel.

The method may further include forming a light propagating tube between the first and second electrodes on the second insulation layer.

The method may further include forming a reflective layer surrounding the light waveguide.

The method may further include forming a plurality of tetrodes for measuring bio-signals by cutting the first through third insulation layer by a laser.

The method may further include forming a plurality of tetrodes for measuring bio-signals by patterning the first through third insulation layers via a photolithography process.

End surfaces of the first through fourth electrodes may have square shapes or circular shapes.

The first through fourth electrodes may be arranged in a square array shape.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1A:
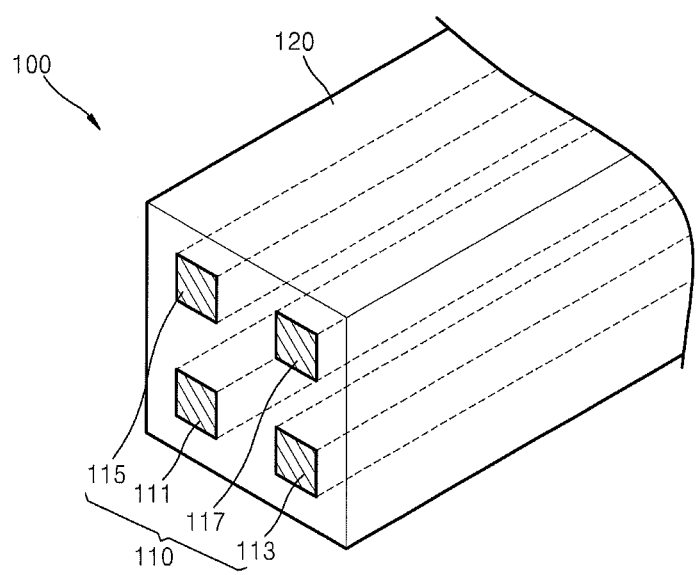
FIG. 1A is a schematic perspective view of a tetrode for measuring bio-signals according to an embodiment of the present invention.

Hereinafter, the present invention will be described in detail by explaining preferred embodiments of the invention with reference to the attached drawings. Like reference numerals in the drawings denote like elements. In the drawings, the thicknesses of layers and regions may be exaggerated for clarity.

Figure 1B:
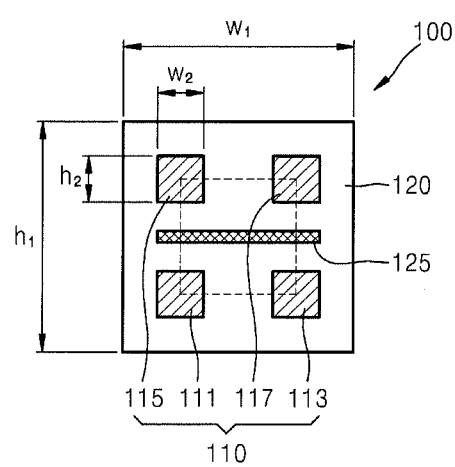
FIG. 1B is a schematic front view of the tetrode for measuring bio-signals shown in FIG. 1A.

FIG. 1A is a schematic perspective view of a tetrode 100 for measuring bio-signals according to an embodiment of the present invention, and FIG. 1B is a schematic front view of the tetrode 100 for measuring bio-signals.

Referring to FIGS. 1A and 1B, the tetrode 100 for measuring bio-signals has an extended shape in a lengthwise direction thereof, and may include at least four electrodes 110 that are arranged apart from each others and an insulation layer 120 which surrounds the electrodes 110 to insulate the electrodes 110 from each others.

The electrodes 110 may include at least four electrodes, e.g., first through fourth electrodes 111, 113, 115, and 117. The electrodes 110 may extend in the lengthwise direction. First end surfaces of the electrodes 110 may be exposed to measure bio-signals. Since the tetrode 100 includes the at least four electrodes 110, the tetrode 100 may precisely detect locations from which the bio-signals are transmitted. In other words, a particular neuron from which a bio-signal is transmitted may be known precisely. Therefore, the tetrode 100 may easily and precisely perform single unit recording. Furthermore, second end surfaces of the electrodes 110 may be connected to an electrical circuit (not shown), so that the bio-signals input by the electrodes 110 may be analyzed. Therefore, the tetrode 100 may be used in various fields of brain research, such as brain computer interface (BCI), deep brain stimulation (DBS), etc.

Each end surface of the electrodes 110 may have a polygonal shape or a circular shape, e.g., a square shape. Width w2 and height h2 of the electrode 110 may be from several μm to hundreds of μm, and the electrodes 110 may be fabricated via a micro electromechanical system (MEMS) process. For example, the width w2 and the height h2 of the electrode 110 may be from about 1 μm to about 200 μm, and more particularly, from about 5 μm to about 50 μm. Furthermore, the width w2 and the height h2 of the electrode 110 may be identical to each other. Meanwhile, the electrode 110 may be fabricated in a nano electromechanical system (NEMS) operation to have the width w2 and the height h2 from several nm to about hundreds of nm. Therefore, since the tetrode 100 according to the present invention has a sufficiently small size, the tetrode 100 may be inserted even into a small living body and may prevent surrounding cells from being damaged during insertion.

The electrodes 110 may be arranged apart from each other and may also be symmetrically arranged around the center of the tetrode 100. The electrodes 110 may be arranged in a polygonal array shape. For example, in a case where the electrodes 110 includes first through fourth electrodes 111, 113, 115, and 117, the electrodes 110 may be arranged in a square shape as shown in FIG. 1B. If the electrodes 110 is arranged in a square shape, each electrode may precisely measure magnitude, direction, and timing of bio-signals.

The electrodes 110 may contain conductive materials, such as metals, conductive polymers, conductive oxides, etc. The electrodes 110 may be formed of Cu, Al, Au, Ag, Cr, Ni, Mo, Ti, Pt, or an alloy thereof, for example. Furthermore, the electrodes 110 may be formed of thiophene, PEDOT, $TiO_2$, $IrO_x$, etc. Meanwhile, at least one electrode from among the electrodes 110 may apply electrical stimulation to cells constituting the living body, e.g., neurons. Alternatively, another electrode other than the four electrodes 110 may be further arranged to apply electrical stimulation to cells constituting the living body, e.g., neurons. The other electrode may be arranged at the center of the four electrodes 110.

The insulation layer 120 may be formed to surround each of the electrodes 110. Therefore, the insulation layer 120 electrically insulates the electrodes 110 from each others and separates the electrodes 110 apart from each others by a constant interval. In other words, the insulation layer 120 may maintain a shape in which the electrodes 110 are arranged, e.g., a square shape.

The end surface of the insulation layer 120 may have a polygonal shape or a circular shape, e.g., a square shape. Width w1 and height h1 of the insulation layer 120 may be from several μm to hundreds of μm. For example, width w1 and height h1 of the insulation layer 120 may be from about 10 μm to about 500 μm, and more particularly, from about 20 μm to about 70 μm. Furthermore, the width w1 and the height h1 of the insulation layer 120 may be identical to each other. Meanwhile, the insulation layer 120 may be fabricated via a NEMS process to have the width w1 and the height h1 from several nm to about hundreds of nm. Therefore, since the tetrode 100 has a sufficiently small size, the tetrode 100 according to the present invention may be inserted even into a small living body and may prevent surrounding cells from being damaged during insertion.

The insulation layer 120 may be formed of a biocompatible polymer or a flexible polymer. The insulation layer 120 may be formed of polyimide or PDMS, for example. Therefore, the tetrode 100 according to the present invention has superior biocompatibility as compared to a silicon-based electrode and is capable of measuring bio-signals for an extended period of time. Furthermore, the tetrode 100 according to the present invention is flexible, and thus it is unlikely that the tetrode 100 according to the present invention breaks during active movements of a living body. Meanwhile, at least one supporting unit 125 may be further arranged in the insulation layer 120 for maintaining hardness of the tetrode 100. The supporting units 125 may be arranged between the first through fourth electrodes 111, 113, 115, and 117 in parallel to the first through fourth electrodes 111, 113, 115, and 117. End surface of the supporting unit 125 may have a polygonal shape or a circular shape, e.g., a rectangular shape or a square shape. Furthermore, the supporting units 125 may be formed of $SiO_2$, SU-8, SiN, etc.

Figure 2:
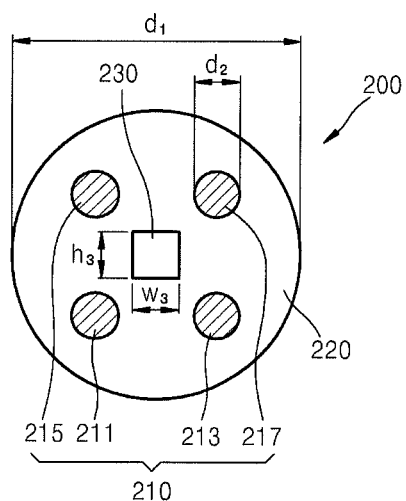
FIG. 2 is a schematic front view of a tetrode according to another embodiment of the present invention.

FIG. 2 is a schematic front view of a tetrode 200 according to another embodiment of the present invention. Hereinafter, differences between the tetrode 100 shown in FIGS. 1A and 1B and the tetrode 200 according to the present embodiment will be described in detail.

Referring to FIG. 2, the tetrode 200 for measuring biosignals extends in a lengthwise direction thereof, that is, a body insertion direction, and may include at least four electrodes 210 that are arranged apart from each others and an insulation layer 220 which surrounds the electrodes 210 to insulate the electrodes 210 from each others. Furthermore, the tetrode 200 may further include a channel 230 interposed between the electrodes 210.

The electrodes 210 may include at least four electrodes, e.g., first through fourth electrodes 211, 213, 215, and 217. Each end surface of the electrodes 210 may have a a circular shape, and a diameter d2 of the electrode 210 may be from several μm to hundreds of μm. For example, the diameter d2 of the electrode 210 may be from about 1 μm to about 200 μm, and more particularly, from about 5 μm to about 50 μm. Meanwhile, the electrode 210 may be fabricated via a MEMS process to have the diameter d2 from several μm to about hundreds of μm. Therefore, since the tetrode 200 according to the present invention has a sufficiently small size, the tetrode 200 may be inserted even into a small living body and may prevent surrounding cells from being damaged during insertion. Furthermore, the electrodes 210 may be symmetrically arranged in a polygonal array shape. For example, as shown in FIG. 2, the electrodes 210 may be arranged in a square shape.

The insulation layer 220 may be formed to surround each of the electrodes 210. The end surface of the insulation layer 220 may have a circular shape, and diameter d1 of the insulation layer 220 may be from several μm to hundreds of μm. For example, the diameter d1 of the insulation layer 220 may be from about 10 μm to about 500 μm, and more particularly, from about 20 μm to about 70 μm. Meanwhile, the insulation layer 220 may be fabricated via a NEMS process to have the diameter d1 from several nm to about hundreds of nm. Therefore, since the tetrode 200 has a sufficiently small size, the tetrode 200 according to the present invention may be inserted even into a small living body and may prevent surrounding cells from being damaged during insertion.

Furthermore, the channel 230 may be arranged in a portion of the insulation layer 220 and may extend in the body insertion direction of the tetrode 200, that is, the lengthwise direction of the tetrode 200. The channel 230 may be formed in parallel to the electrodes 210. Furthermore, the channel 230 may be formed between the electrodes 210 and at the center of the insulation layer 220. A predetermined drub may be transmitted to neurons via the channel 230. A first end surface of the channel 230 may be open to transmit a drug to neurons, and a second end surface of the channel 230 may be connected to a micro pump (not shown) and a drug chamber (not shown), for example.

End surfaces of the channel 230 may have a polygonal shape or a circular shape, e.g., a square shape or a rectangular shape. Width w3 and height h3 of the channel 230 may be from several μm to hundreds of μm. For example, the width w3 and the height h3 of the channel 230 may be from about 1 μm to about 200 μm, and more particularly, from about 5 μm to about 50 μm. Furthermore, the width w3 and the height h3 of the channel 230 may be identical to each other. Meanwhile, the channel 230 may be fabricated in a nano electromechanical system (NEMS) operation to have the width w3 and the height h3 from several nm to about hundreds of nm.

Figure 3:
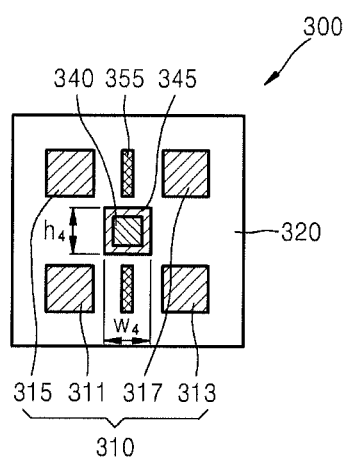
FIG. 3 is a schematic front view of a tetrode according to another embodiment of the present invention.

FIG. 3 is a schematic front view of a tetrode 300 according to another embodiment of the present invention. Hereinafter, differences between the tetrodes 100 and 200 shown in FIGS. 1A, 1B, and 2 and the tetrode 300 according to the present embodiment will be described in detail.

Referring to FIG. 3, the tetrode 300 for measuring biosignals extends in a a lengthwise direction thereof, and may include at least four electrodes 310 that are arranged apart from each others and an insulation layer 320 which surrounds the electrodes 310 to insulate the electrodes 310 from each others. Furthermore, the tetrode 300 may further include light waveguide 340 interposed between the electrodes 310.

The electrodes 310 may include at least four electrodes, e.g., first through fourth electrodes 311 and 313, 315, and 317. Each end surface of the electrodes 310 may have a square shape, and width and height of the electrode 310 may be from several μm to hundreds of μm, and the electrode 310 may be fabricated via a NEMS process to have the width and the height from several nm to about hundreds of nm. Furthermore, the electrodes 310 may be symmetrically arranged in a polygonal array shape. For example, as shown in FIG. 3, the electrodes 310 may be arranged in a square shape.

The insulation layer 320 may be formed to surround each of the electrodes 310. The end surface of the insulation layer 320 may have a square shape, and width and height of the insulation layer 320 may be from several μm to hundreds of μm. Meanwhile, the insulation layer 320 may be fabricated via a NEMS process to have the width and the height from several nm to about hundreds of nm. Therefore, since the tetrode 300 has a sufficiently small size, the tetrode 300 according to the present invention may be inserted even into a small living body and may prevent surrounding cells from being damaged during insertion.

Furthermore, the light waveguide 340 may be arranged in a portion of the insulation layer 320 and may extend in a lengthwise direction of the tetrode 300, that is, the body insertion direction. The light waveguidelight waveguide 340 may be formed in parallel to the electrodes 310. Furthermore, the light waveguide 340 may be formed between the electrodes 310 and at the center of the insulation layer 320. Light may be transmitted to neurons via the light waveguide 340. The tetrode 300 according to the present embodiment may emit light of a predetermined intensity to a precise location. Therefore, the tetrode 300 according to the present embodiment may be also used in research in the opto-genetic field. A first end surface of the light waveguide 340 may be open to emit a predetermined light to neurons, whereas a second end surface of the light waveguide 340 may be connected to a light source (not shown), such as a laser.

The light waveguide 340 may be formed of a transparent material capable of transmitting light. For example, the light waveguide 340 may be formed of SiN, SiON, SU-8, etc. Alternatively, the light waveguide 340 may be formed of a glass material or a plastic material and may be doped with a gain medium. The gain medium may be a rare-earth element, e.g., Pr, Tb, Dy, Nd, Pm, Sm, Eu, Gd, Dy, Ho, Er, Tm, Yb, or a combination thereof.

End surfaces of the light waveguide 340 may have a polygonal shape or a circular shape, e.g., a square shape or a rectangular shape. Width w4 and height h4 of the light waveguide 340 may be from several μm to hundreds of μm. For example, the width w4 and the height h4 of the light waveguide 340 may be from about 1 μm to about 90 μm, and more particularly, from about 5 μm to about 50 μm. Furthermore, the width w4 and the height h4 of the light waveguide 340 may be identical to each other.

Furthermore, a reflective layer 345 may surround the light waveguide 340. The reflective layer 345 may prevent light from leaking outside by reflecting light transmitting through the light waveguide 340. Therefore, an efficiency of transmitting light to neurons may be improved, and a light source with lower output may be employed. The reflective layer 345 may contain a metal with excellent light reflectivity, e.g., Al, Ni, Cr, Cu, Au, Ag, etc. Furthermore, the reflective layer 345 may be formed of a material having relatively small refractive index as compared to a material constituting the light waveguide 340. The reflective layer 345 may be formed of a silica glass, a glass with a low refractive index, or a polymer. The reflective layer 345 may be formed of an oxide, e.g., $SiO_2$. Meanwhile, the light waveguide 340 and the reflective layer 345 may be formed in the channel 230 shown in FIG. 2. Furthermore, at least one supporting unit 355 may be further arranged in the insulation layer 320 for maintaining hardness of the tetrode 300. The supporting units 355 may be arranged between the first through fourth electrodes 311 and 313, 315, and 317 in parallel to the first through fourth electrodes 311 and 313, 315, and 317. End surface of the supporting unit 355 may have a polygonal shape or a circular shape, e.g., a rectangular shape or a square shape. Furthermore, the supporting units 355 may be formed of $SiO_2$, SU-8, SiN, etc. FIG. 3 shows an example in which the two supporting units 355 are arranged between the first and second electrodes 311 and 313 and between the third and fourth electrodes 315 and 317, respectively.

Figure 4A:
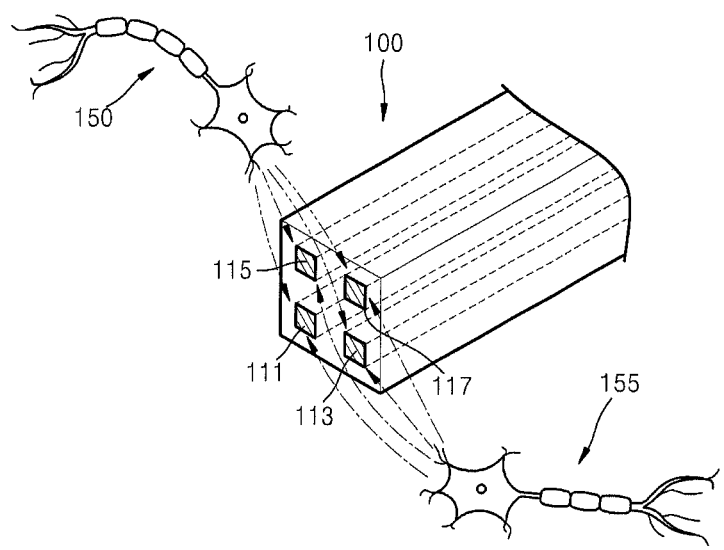
FIGS. 4A-4C schematically show a method of measuring bio-signals from neurons by the tetrode according to the present invention.
Figure 4B:
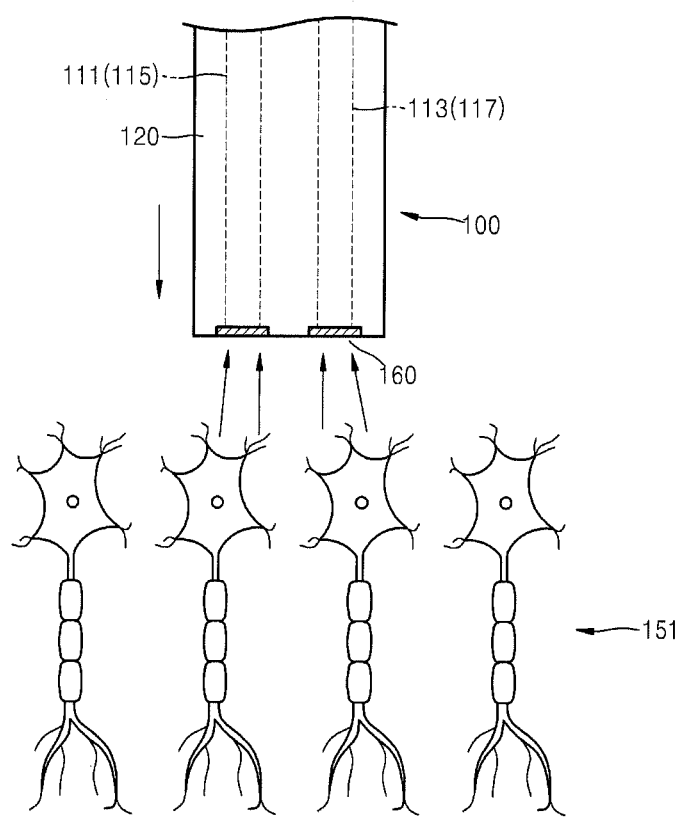

FIGS. 4A and 4B schematically show a method of measuring bio-signals from neurons by the tetrode 100 according to the present invention.

Referring to FIG. 4A, the tetrode 100 may receive bio-signals from first and second neurons 150 and 155, which are apart from the tetrode 100 by the same distance. Although the first and second neurons 150 and 155 are apart from the tetrode 100 by a same distance, intensities, directions, and times of bio-signals received by the first through fourth electrodes 111, 113, 115, 117 differ from each others. Therefore, the tetrode 100 may precisely figure out locations of the first and second neurons 150 and 155 and may determine neurons from which particular bio-signals are measured.

Figure 4C:
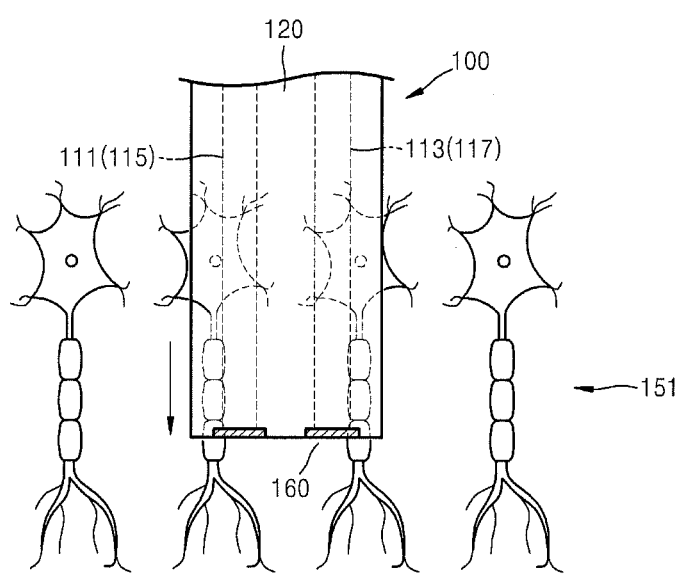

Referring to FIGS. 4B and 4C, the tetrode 100 may move in the direction indicated by the arrow and measure bio-signals from neurons 151. In other words, the tetrode 100 may measure bio-signals from exposed end surfaces of the first through fourth electrodes 111, 113, 115, and 117. Therefore, the tetrode 100 may measure bio-signals according to depths to which the tetrode 100 is inserted into a living body. For example, the tetrode 100 may measure bio-signals from a thin brain region including a single layer of neurons. Meanwhile, a metal layer 160 may be further arranged on the exposed end surfaces of the first through fourth electrodes 111, 113, 115, and 117. The metal layer 160 may improve biocompatibility and adjust impedances of the first through fourth electrodes 111, 113, 115, and 117. The metal layer 160 may be formed of Au, Ag, Cu, Al, or an alloy thereof.

Figure 5:
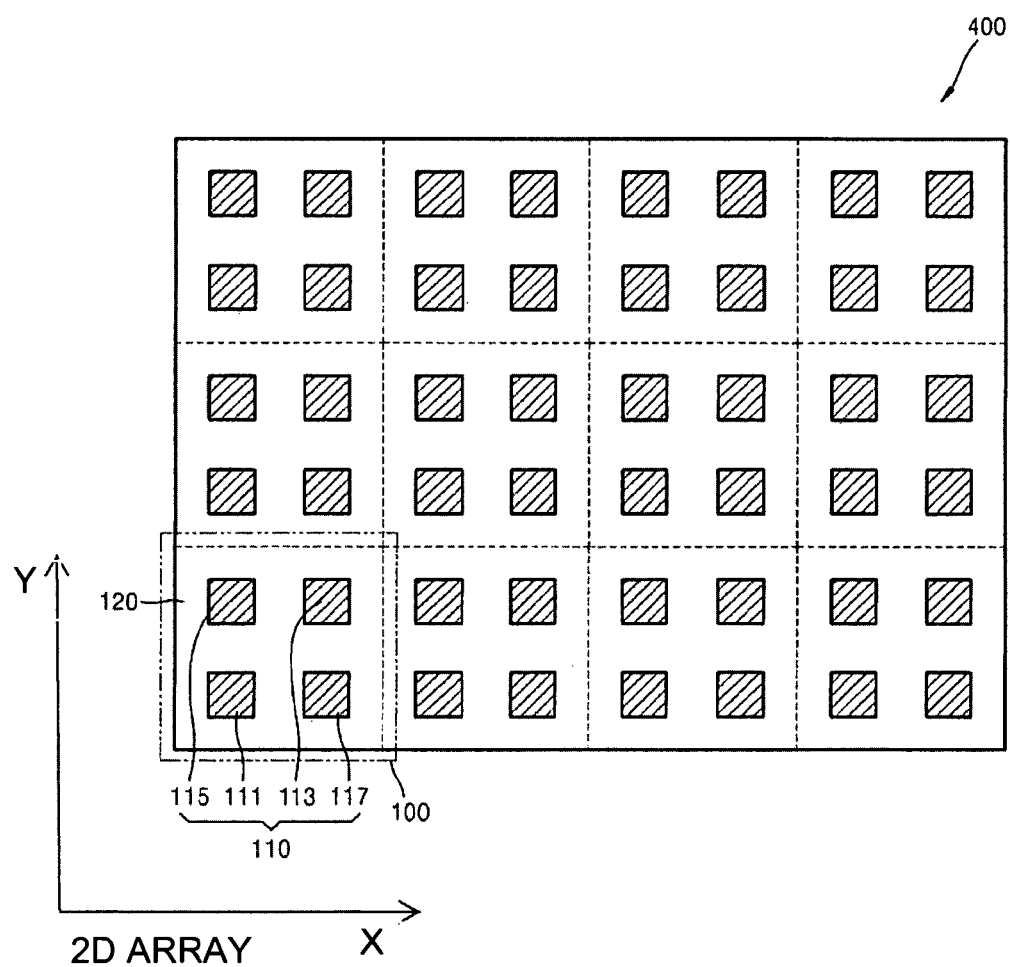
FIG. 5 is a schematic front view of a tetrode array 400 for measuring bio-signals, according to an embodiment of the present invention.

FIG. 5 is a schematic front view of a tetrode array 400 for measuring bio-signals, according to an embodiment of the present invention.

Referring to FIG. 5, the tetrode array 400 according to the present embodiment includes a plurality of the tetrodes 100 described above, where the plurality of tetrodes 100 may be arranged in a 2D array shape. In the tetrode array 400, the plurality of tetrodes 100 may be arranged in a m×n array shape (where m and n are natural numbers). Although FIG. 5 shows that the twelve tetrode 100 are arranged in a 3×4 array shape, the present invention is not limited thereto, and the tetrode array 400 may have any of various arrangements. Since the tetrode array 400 includes the plurality of tetrode 100, the tetrode array 400 is capable of simultaneously measuring bio-signals from a plurality of neurons distributed in a large area.

FIGS. 6A through 6H are schematic diagrams showing a process for manufacturing the tetrode 300 and an array 400' thereof.

Figure 6A:
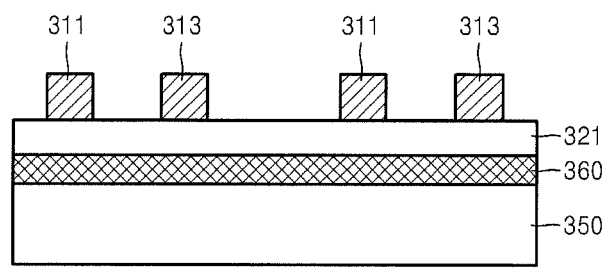
FIGS. 6A through 6H are schematic diagrams showing a process for manufacturing the tetrode and an array thereof.

Referring to FIG. 6A, a sacrificial layer 360 may be formed on a semiconductor wafer 350. The semiconductor wafer 350 may be a silicon wafer, for example, whereas the sacrificial layer 360 may contain silicon oxide, silicon nitride, zirconium oxide, phosphor-silicate glass (PSG), borophosphor-silicate glass (BPSG), etc. Furthermore, the sacrificial layer 360 may be formed of a metal, a solid solution, an oxide, a nitride, or a high-temperature organic material, which may be chemically etched. For example, the sacrificial layer 360 may be formed of a chrome-copper alloy.

Next, a first insulation layer 321 may be formed on the sacrificial layer 360, and then a plurality of electrodes may be formed on the first insulation layer 321. For example, at least one first electrode 311 and at least one second electrode 313 apart from the first electrode 311 may be formed on the first insulation layer 321. The first insulation layer 321 may be formed of a biocompatible polymer or a flexible polymer. The first insulation layer 321 may be formed of polyimide or PDMS, for example. The first insulation layer 321 may be formed by depositing or spin-coating a polymer as stated above. Furthermore, the first insulation layer 321 may be cured after being deposited or spin-coated.

The first and second electrodes 311 and 313 may contain conductive materials, such as metals, conductive polymers, conductive oxides, etc. The first and second electrodes 311 and 313 may be formed of Cu, Al, Au, Ag, Cr, Ni, Mo, Ti, Pt, or an alloy thereof, for example. Furthermore, the first and second electrodes 311 and 313 may be formed of thiophene, PEDOT, $TiO_2$, $IrO_x$, etc. For example, the first and second electrodes 311 and 313 may be formed by patterning via a photolithography process and plating or depositing conductive materials on the first insulation layer 321. In a case where the first and second electrodes 311 and 313 are formed via a plating process, a seed layer may be formed, and then electrodes may be formed on the seed layer. Furthermore, if the first and second electrodes 311 and 313 are formed via a plating process, first end surfaces of the first and second electrodes 311 and 313 may be polished flat, where the first end surfaces of the first and second electrodes 311 and 313 are end surfaces inserted into a living body.

Figure 6B:
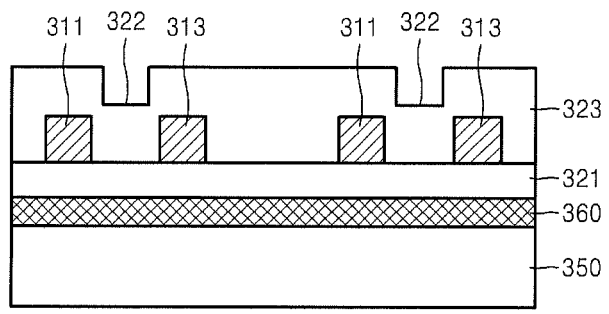

Next, referring to FIG. 6B, a second insulation layer 323 may be formed on the first insulation layer 321 and the first and second electrodes 311 and 313. The second insulation layer 323 may be formed of a biocompatible polymer or a flexible polymer. The second insulation layer 323 may be formed of polyimide or PDMS, for example. The second insulation layer 323 may be formed by depositing or spin-coating a polymer as explained above and curing the polymer. A channel 322 may be formed between the first and second electrodes 311 and 313. The channel 322 may become a path along which a predetermined drug to be injected to a neuron flows. Meanwhile, the light waveguide 340 may be formed in the channel 322 in an operation described below.

Figure 6C:
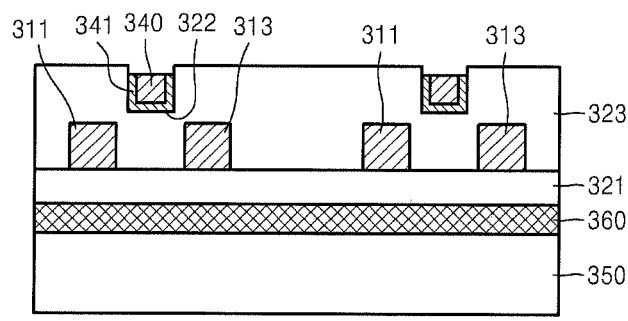

Referring to FIG. 6C, a first reflective layer 341 may be formed in the channel 322, and the light waveguide 340 may be formed in the first reflective layer 341. The first reflective layer 341 may contain a metal with excellent light reflectivity, e.g., Al, Ni, Cr, Cu, Au, Ag, etc. Furthermore, the first reflective layer 341 may be formed of a material having relatively small refractive index as compared to a material constituting the light waveguide 340. The first reflective layer 341 may be formed of a silica glass, a glass with a low refractive index, or a polymer, for example. The light waveguide 340 may be formed of a transparent material capable of transmitting light. For example, the light waveguide 340 may be formed of SiN, SiON, SU-8, etc. Alternatively, the light waveguide 340 may be formed of a glass material or a plastic material and may be doped with a gain medium. The gain medium may be a rare-earth element, e.g., Pr, Tb, Dy, Nd, Pm, Sm, Eu, Gd, Dy, Ho, Er, Tm, Yb, or a combination thereof. Meanwhile, the light waveguide 340 may be formed on the flat second insulation layer 323 without forming the channel 322 in the second insulation layer 323. Next, a third insulation layer (325 of FIG. 6D) may be formed on the second insulation layer 323 to cover the light waveguide 340.

Figure 6D:
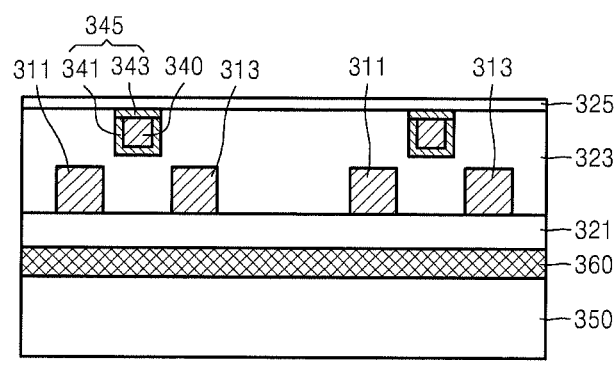

Referring to FIG. 6D, a second reflective layer 343 may be formed on the light waveguide 340. The second reflective layer 343 may be formed of a same material as the first reflective layer 341. The first and second reflective layers 341 and 343 may form the reflective layer 345 and surround the light waveguide 340. The reflective layer 345 may prevent light from being leaked to outside by reflecting light passing through the light waveguide 340. Next, the third insulation layer 325 may be formed on the second reflective layer 343 and the second insulation layer 323. The third insulation layer 325 may be formed of the same material as the first and second insulation layers 321 and 323 and may be formed by depositing or spin-coating a polymer as explained above and curing the polymer.

Figure 6E:
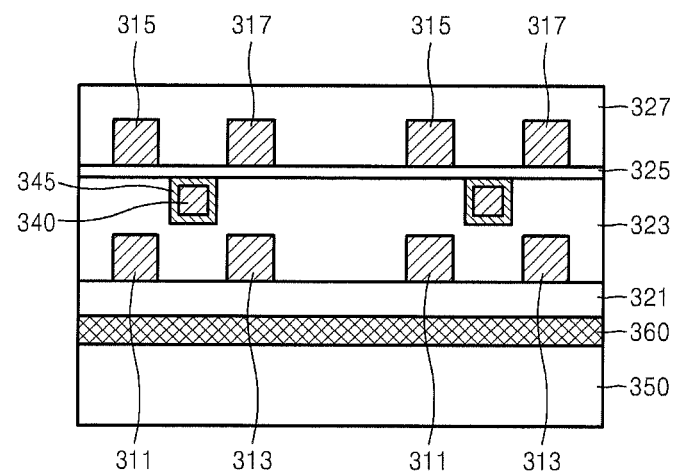

Referring to FIG. 6E, a plurality of electrodes may be formed on the third insulation layer 325. For example, at least one third electrode 315 and at least one fourth electrode 317 apart from the third electrode 315 may be formed on the third insulation layer 325. Next, a fourth insulation layer 327 may be formed on the third insulation layer 325 and the third and fourth electrode 315 and 317. The third and fourth electrode 315 and 317 may contain conductive materials, such as metals, conductive polymers, conductive oxides, etc. The third and fourth electrode 315 and 317 may be formed of Cu, Al, Au, Ag, Cr, Ni, Mo, Ti, Pt, or an alloy thereof, for example. Furthermore, the third and fourth electrode 315 and 317 may be formed of thiophene, PEDOT, $TiO_2$, $IrO_x$, etc. For example, the third and fourth electrode 315 and 317 may be formed by patterning via a photolithography process and plating or depositing conductive materials on the third insulation layer 325. If the third and fourth electrode 315 and 317 are formed via a plating process, a seed layer may be formed, and then electrodes may be formed on the seed layer. Furthermore, if the third and fourth electrode 315 and 317 are formed via a plating process, first end surfaces of the third and fourth electrode 315 and 317 may be polished flat, where the first end surfaces of the third and fourth electrode 315 and 317 are end surfaces inserted into a living body. Meanwhile, in the photolithography process, both a stepper type exposer and an aligner type exposer may be used.

The fourth insulation layer 327 may contain the same material as the first through third and second insulation layers 321, 323, and 325. The fourth insulation layer 327 may be formed by depositing or spin-coating a polymer as presented above. Furthermore, the fourth insulation layer 327 may be cured after being deposited or spin-coated Referring to FIG. 6F, a plurality of the tetrodes 300 may be formed by partially removing first through fourth insulation layer 321, 323, 325, and 327 between the second electrode 313 and the first electrode 311 which constitute each of the tetrode 300. For example, the plurality of tetrodes 300 may be formed by cutting the first through fourth insulation layer 321, 323, 325, and 327 using a laser. The first through fourth insulation layer 321, 323, 325, and 327 may be cut by a femtosecond laser. Furthermore, in a case where the first through fourth insulation layer 321, 323, 325, and 327 contain a photosensitive polymer, the plurality of tetrodes 300 may be formed by patterning the first through fourth insulation layer 321, 323, 325, and 327 via a photolithography process. Meanwhile, the first through fourth insulation layer 321, 323, 325, and 327 may constitute the insulation layer 320.

Figure 6F:
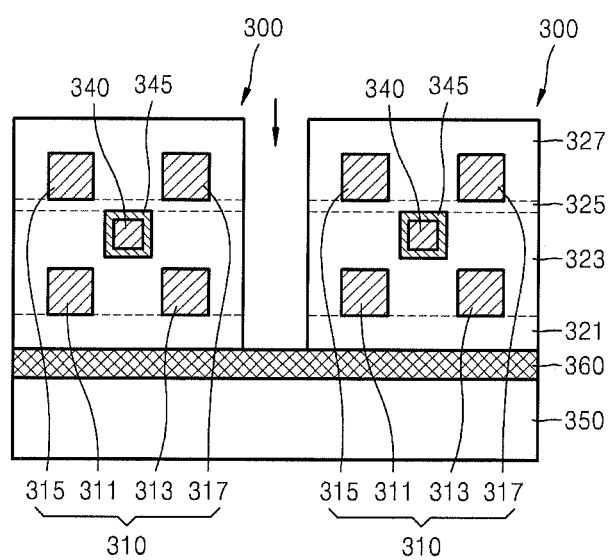
Figure 6G:
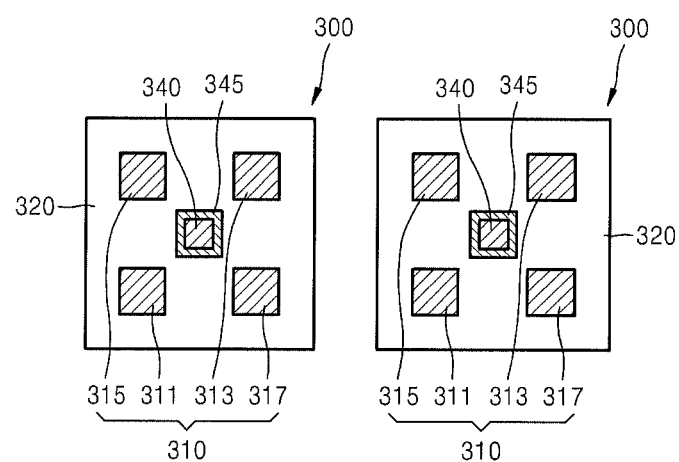

Next, referring to FIG. 6G, the plurality of tetrodes 300 may be separated from the semiconductor wafer (350 of FIG. 6F) by removing the sacrificial layer (360 of FIG. 6F). The sacrificial layer 360 may be removed via an etching process.

Figure 6H:
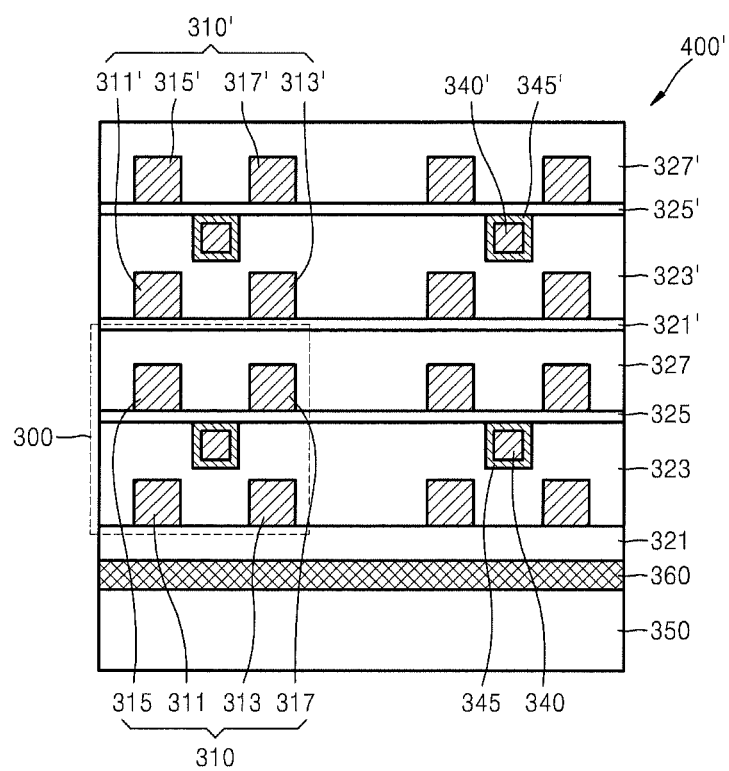

Meanwhile, referring to FIG. 6F, before the plurality of tetrodes 300 are formed by partially removing the first through fourth insulation layer 321, 323, 325, and 327, the operations shown in FIGS. 6A through 6E, which include formation of a first insulation layer 321' on the fourth insulation layer 327 and formation of the first and second electrodes 311' and 313' on the first insulation layer 321', may be performed at least once. Accordingly, by repeatedly performing the operations shown in FIGS. 6A through 6E, a tetrode array 400' may be formed. Although FIG. 6H shows that the four tetrodes 300 are arranged in a 2×2 array shape, the present invention is not limited thereto, and the tetrode array 400' may have any of various arrangements.

The methods for manufacturing the tetrode 300 for measuring bio-signals and the array 400' thereof may be performed via a MEMS process. Therefore, compared to the conventional method in which four wires are mechanically twisted, the first through fourth electrodes 311, 313, 315, and 317 may be uniformly arranged, and short circuits due to contacts between the electrodes may be prevented. Furthermore, the tetrode 300 may be manufactured to a small size from several μm to hundreds of μm, and thus damages to living body may be prevented. Furthermore, the tetrode 300 may be manufactured to a size from about several nm to hundreds of nm.

In the present embodiment, at least the one channel 322 is formed in the second insulation layer 323, the first reflective layer 341 and the light waveguide 340 are formed in the channel 322 in the order stated, and the second reflective layer 343 is formed on the light waveguide 340. However, the present invention is not limited thereto. Instead of using the channel 322, the reflective layer 345 and the light waveguide 340 may be formed on the second insulation layer 323. For example, the reflective layer may be formed on the top surface of the second insulation layer 323, the light waveguide 340 may be formed on the top surface of the reflective layer, and reflective layers may be formed on the side surfaces and the top surface of the light waveguide, and thus, the light waveguide 340 and the reflective layer 345 may be formed on the second insulation layer 323.

Figure 7A:
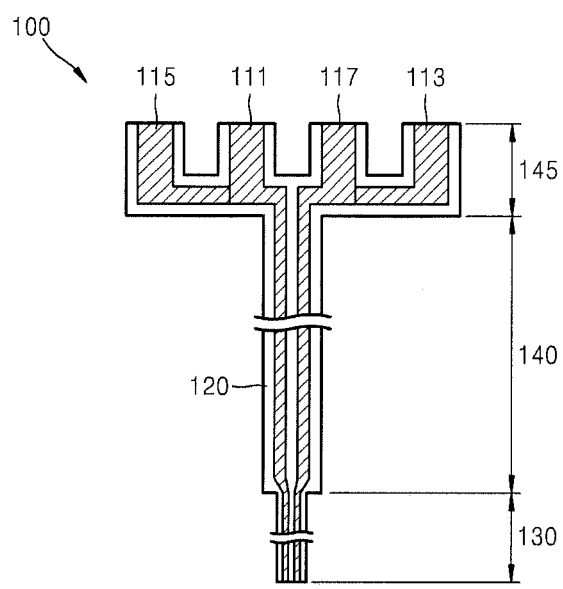
FIG. 7A is a schematic plan view of the tetrode.
Figure 7B:
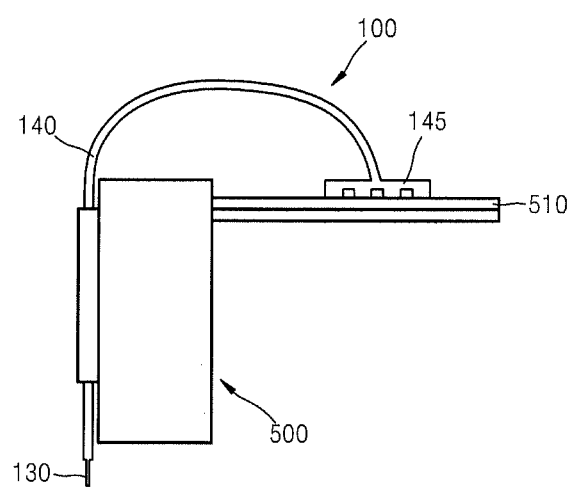
FIG. 7B shows an example of application of the tetrode.

FIG. 7A is a schematic plan view of the tetrode 100, and FIG. 7B shows an example of application of the tetrode 100.

Referring to FIGS. 7A and 7B, the tetrode 100 may include a body insertion unit 130, a fixing unit 140, and a circuit connecting unit 145. The overall shape of the tetrode 100 may be a "T"-like shape. In other words, the body insertion unit 130 and the fixing unit 140 may extend in a lengthwise direction thereof. Furthermore, the circuit connecting unit 145 may be formed to spread from the fixing unit 140, such that the first through fourth electrodes 111, 113, 115, and 117 are farther apart from each other.

As described above with reference to FIGS. 1A and 1B, the body insertion unit 130 may include the first through fourth electrodes 111, 113, 115, and 117 and the insulation layer 120 surrounding the first through fourth electrodes 111, 113, 115, and 117. The body insertion unit 130 is a portion directly inserted into a living body, where height and width of the body insertion unit 130 may be from several nm to hundreds of μm to prevent damages to living cells. Furthermore, length of the body insertion unit 130 may be from several mm to hundreds of mm, e.g., from about 1 mm to about 100 mm.

The fixing unit 140 is a portion fixed to the micro driving unit 500. The micro driving unit 500 includes a motor, so that the tetrode 100 may be inserted to a living body. The micro driving unit 500 may insert the tetrode 100 to a living body by a fine unit from several nm to several μm. The first through fourth electrodes 111, 113, 115, and 117 included in the fixing unit 140 may be same-sized or larger as compared to the first through fourth electrodes 111, 113, 115, and 117 included in the body insertion unit 130. The fixing unit 140 may be larger than the body insertion unit 130, such that the fixing unit 140 is easily fixed to the micro driving unit 500. For example, width of the fixing unit 140 may be from several μm to hundreds of mm. Furthermore, length of the fixing unit 140 may be from several mm to hundreds of mm, e.g., from about 10 mm to about 50 mm.

The circuit connecting unit 145 may interconnect the electrical circuit 510 included in the micro driving unit 500 and the tetrode 100. The electrical circuit 510 may analyze biosignals received from the first through fourth electrodes 111, 113, 115, and 117. For easier connection to the electrical circuit 510, the first through fourth electrodes 111, 113, 115, and 117 included in the circuit connecting unit 145 may be same-sized as or larger than the first through fourth electrodes 111, 113, 115, and 117 included in the fixing unit 140. Furthermore, for easier connection to the electrical circuit 510, width of the circuit connecting unit 145 may be from several mm to hundreds of mm. Furthermore, shape of end surfaces of the first through fourth electrodes 111, 113, 115, and 117 included in the body insertion unit 130 may be squares, whereas shapes of end surfaces of the first through fourth electrodes 111, 113, 115, and 117 included in the fixing unit 140 and the circuit connecting unit 145 may be squares or rectangles.

Meanwhile, as shown in FIG. 7B, since the fixing unit 140 may be bent as being fixed to the micro driving unit 500 and tetrode 100 is flexible, the circuit connecting unit 145 may be connected to the electrical circuit 510 included in the micro driving unit 500.

Figure 8A:
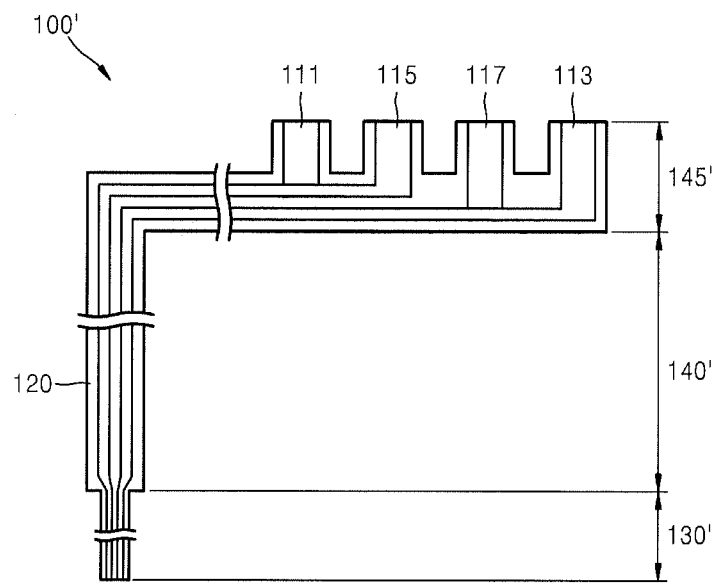
FIG. 8A is a schematic plan view of the tetrode.
Figure 8B:
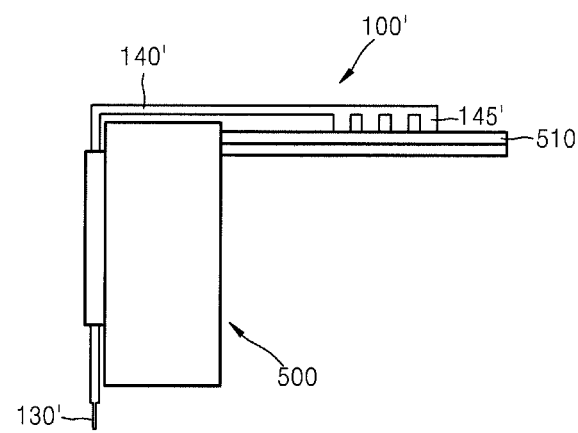
FIG. 8B shows an example of application of the tetrode.

FIG. 8A is a schematic plan view of the tetrode 100', and FIG. 8B shows an example of application of the tetrode 100'.

Referring to FIGS. 8A and 8B, the tetrode 100' may include a body insertion unit 130', a fixing unit 140', and a circuit connecting unit 145'. The overall shape of the tetrode 100' may be a "L"-like shape. In other words, the body insertion unit 130' and the fixing unit 140' may extend in the lengthwise direction thereof, and the circuit connecting unit 145' may be bent by a predetermined angle with respect to the fixing unit 140'. For example, the circuit connecting unit 145' may be bent to be perpendicular to the fixing unit 140'. Furthermore, the circuit connecting unit 145' may be formed to spread from the fixing unit 140, such that the first through fourth electrodes 111, 113, 115, and 117 are farther apart from each other As described above with reference to FIGS. 1A and 1B, the body insertion unit 130' may include the first through fourth electrodes 111, 113, 115, and 117 and the insulation layer 120 surrounding the first through fourth electrodes 111, 113, 115, and 117. The body insertion unit 130' is a portion directly inserted into a living body, and height and width of the body insertion unit 130' may be from several nm to hundreds of μm to prevent damages to living cells. Furthermore, length of the body insertion unit 130' may be from several mm to hundreds of mm, e.g., from about 1 mm to about 10 mm.

The fixing unit 140' is a portion fixed to the micro driving unit 500. The micro driving unit 500 includes a motor, so that the tetrode 100' may be inserted to a living body. The micro driving unit 500 may insert the tetrode 100' to a living body by a fine unit from several nm to several μm. The first through fourth electrodes 111, 113, 115, and 117 included in the fixing unit 140' may be same-sized or larger as compared to the first through fourth electrodes 111, 113, 115, and 117 included in the body insertion unit 130'. The fixing unit 140' may be larger than the body insertion unit 130', such that the fixing unit 140' is easily fixed to the micro driving unit 500. For example, width of the fixing unit 140' may be from dozens of μm to several mm. Furthermore, length of the fixing unit 140' may be from several mm to dozens of mm, e.g., from about 10 mm to about 50 mm.

The circuit connecting unit 145' may interconnect the electrical circuit 510 included in the micro driving unit 500 and the tetrode 100'. The electrical circuit 510 may analyze biosignals received from the first through fourth electrodes 111, 113, 115, and 117. For easier connection to the electrical circuit 510, the first through fourth electrodes 111, 113, 115, and 117 included in the circuit connecting unit 145' may be same-sized as or larger than the first through fourth electrodes 111, 113, 115, and 117 included in the fixing unit 140'. Furthermore, for easier connection to the electrical circuit 510, width of the circuit connecting unit 145' may be from several mm to dozens of mm. Furthermore, shape of end surfaces of the first through fourth electrodes 111, 113, 115, and 117 included in the body insertion unit 130 may be squares, whereas shapes of end surfaces of the first through fourth electrodes 111, 113, 115, and 117 included in the fixing unit 140' and the circuit connecting unit 145' may be squares or rectangles.

Meanwhile, as shown in FIG. 8B, the fixing unit 140' is fixed to the micro driving unit 500, and the circuit connecting unit 145 which extends from the bent portion of the tetrode 100' may be connected to the electrical circuit 510 included in the micro driving unit 500.

Figure 9A:
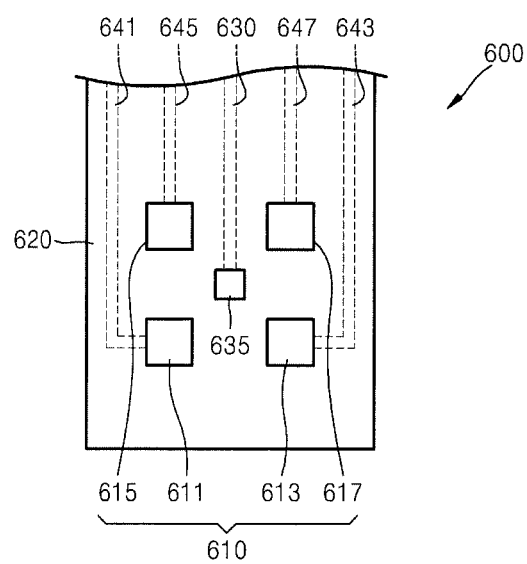
FIGS. 9A and 9B are respectively schematic plan view of tetrodes according to other embodiments of the present invention.
Figure 9B:
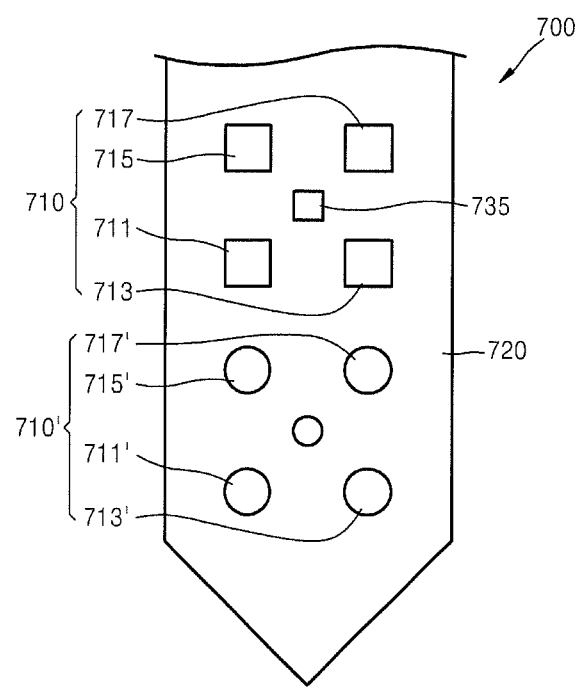

FIGS. 9A and 9B are respectively schematic plan view of tetrodes 600 and 700 according to other embodiments of the present invention.

Referring to FIG. 9A, the tetrode 600 may include at least four electrodes 610, which are exposed in a direction perpendicular to the body insertion direction and are apart from each others, and an insulation layer 620, which insulates the electrodes 610 from each others and supports the electrodes 610. Furthermore, an outlet 635 of a light propagating tube 630 may be further arranged at the center of the electrodes 610.

The electrodes 610 may be formed on the insulation layer 620 and may include at least four electrodes. For example, the electrodes 610 may include first through fourth electrodes 611, 613, 615, and 617. The electrodes 610 may be exposed in a direction perpendicular to the body insertion direction, and the electrodes 610 may be connected to an external electrical circuit (not shown) respectively via electrical wires 641, 643, 645, and 647 which extend in the insulation layer 620 in the direction of body insertion. As described above, the tetrode 600 includes the at least four electrodes 610, thus being capable of precisely determining locations from which biosignals are transmitted. In other words, the tetrode 600 is capable of locating particular neurons from which the biosignals are transmitted. Therefore, the tetrode 600 may easily and precisely perform single unit recording.

The electrodes 610 may have a polygonal shape or a circular shape, e.g., a square. The electrodes 610 may be formed via a MEMS process. The electrodes 610 may be arranged apart from each others. Furthermore, the electrodes 610 may be symmetrically arranged around the outlet 635 of the light waveguide 630. The electrodes 610 may be arranged in a polygonal array shape. For example, if the electrodes 610 includes the first through fourth electrodes 611, 613, 615, and 617, the electrodes 610 may be arranged in a square array shape as shown in FIG. 9A. If the electrodes 610 are arranged in a polygonal array shape, each electrode may precisely measure magnitude, direction, and time of bio-signals.

The electrodes 610 may contain conductive materials, such as metals, conductive polymers, conductive oxides, etc. The electrodes 610 may be formed of Cu, Al, Au, Ag, Cr, Ni, Mo, Ti, Pt, or an alloy thereof, for example. Furthermore, the electrodes 610 may be formed of thiophene, PEDOT, $TiO_2$, $IrO_x$, etc. Meanwhile, at least one electrode from among the electrodes 610 may apply electrical stimulation to cells constituting the living body, e.g., neurons. Alternatively, other electrode other than the four electrodes 610 may be further arranged to apply electrical stimulation to cells constituting the living body, e.g., neurons. The other electrode may be arranged at the center of the four electrodes 610 and may be formed instead of the light waveguide 630.

The insulation layer 620 may be formed to support the electrodes 610 and to surround the electrical wires 641, 643, 645, and 647 connected to the electrodes 610. Therefore, the insulation layer 620 may electrically insulate the electrical wires 641, 643, 645, and 647 from each others. End surface of the insulation layer 620 may extend in the body insertion direction, and the insulation layer 620 may be formed to have a cuboidal shape.

The insulation layer 620 may be formed of a biocompatible polymer or a flexible polymer. The insulation layer 620 may be formed of polyimide or PDMS, for example. Therefore, the tetrode 600 according to the present invention has superior biocompatibility as compared to a silicon-based electrode and is capable of measuring bio-signals for an extended period of time. Furthermore, the tetrode 600 according to the present invention is flexible, and thus, it is unlikely that the tetrode 600 according to the present invention will break during active movements of a living body. Meanwhile, at least one supporting unit 625 may be further arranged in the insulation layer 620 for maintaining hardness of the tetrode 600.

Furthermore, the light waveguide 630 may be arranged in a portion of the insulation layer 620 and may extend in the body insertion direction of the tetrode 600, that is, the lengthwise direction of the tetrode 600. The light waveguide 640 may be formed in parallel to the electrical wires 641, 643, 645, and 647. Furthermore, the light waveguide 640 may be formed between the electrical wires 641, 643, 645, and 647 and at the center of the insulation layer 620. Furthermore, the outlet 635 may be arranged at an end of the light waveguide 630. Light passing through the light waveguide 630 may be transmitted to neurons via the outlet 635. The tetrode 600 according to the present embodiment may emit light of a predetermined intensity to a precise location via the light waveguide 630. Therefore, the tetrode 600 according to the present embodiment may be also used in research in the opto-genetic field.

The light waveguide 630 may be formed of a transparent material capable of transmitting light. For example, the light waveguide 630 may be formed of SiN, SiON, SU-8, etc. Alternatively, the light waveguide 630 may be formed of a glass material or a plastic material and may be doped with a gain medium. The gain medium may be a rare-earth element, e.g., Pr, Tb, Dy, Nd, Pm, Sm, Eu, Gd, Dy, Ho, Er, Tm, Yb, or a combination thereof. End surfaces of the light waveguide 630 may have a polygonal shape or a circular shape, e.g., a square shape or a rectangular shape. Furthermore, a reflective layer (not shown) may surround the light waveguide 630.

Referring to FIG. 9B, the tetrode 700 may include at least four electrodes 710, which are exposed in a direction perpendicular to the body insertion direction and are apart from each others, and an insulation layer 720, which insulates the electrodes 710 from each others and supports the electrodes 710. An outlet 735 of a light propagating tube may be further arranged at the center of the electrodes 710. Furthermore, the tetrode 700 may further include other four electrodes 710' arranged along the body insertion direction, and an outlet 735' of the light waveguide 630 formed at the center of the electrodes 710'.

In other words, the tetrode 700 may include a plurality of sets of the four electrodes 710 and the outlet 735 of a light propagating tube formed between the four electrodes 710. Furthermore, the plurality of sets may be arranged along a body insertion direction. Since each of the plurality of sets is capable of measuring bio-siganls from neurons or emitting light to neurons, the tetrode 700 is capable of simultaneously collecting information from a plurality of neurons. Furthermore, the tetrode 700 may acquire more precise information by measuring bio-signals from a single neuron via the plurality of sets.

As described above, the tetrodes and the arrays thereof are manufactured via a MEMS process. However, the present invention is not limited thereto, and thus, the tetrodes and the arrays thereof may also be manufactured via a NEMS process.

The tetrode according to the present invention includes at least four electrodes. The tetrode may precisely detect locations from which the bio-signals are transmitted. Since the tetrode has a sufficiently small size, the tetrode may be inserted even into a small living body, thereby preventing surrounding cells from being damaged during insertion. Furthermore, the tetrode according to the present invention has superior biocompatibility as compared to a silicon-based electrode and is capable of measuring bio-signals for an extended period of time. The tetrode according to the present invention is flexible, and thus, it is unlikely that the tetrode will break during active movements of a living body. Furthermore, the tetrode may apply not only electrical stimulation to a living body, but also precisely transmit predetermined drugs or light to neurons.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A tetrode for measuring bio-signals, the tetrode comprising:
    at least four electrodes which extend in a lengthwise direction of the tetrode and are apart from each other, the at least four electrodes being exposed only on a front surface of the tetrode, such that a portion of each of the at least four electrodes is exposed at a direction normal to the lengthwise direction of the tetrode; and
    an insulation layer which insulates the electrodes from each other and which has an elongated shaft structure elongated in the lengthwise direction, and,
    wherein the tetrode is inserted into a living body and a diameter of the insulation layer is smaller than or equal to approximately 500 μM.

2. The tetrode of claim 1, wherein first end surfaces of the electrodes are exposed to measure bio-signals.

3. The tetrode of claim 1, wherein first end surfaces of the electrodes have square shapes or circular shapes.

4. The tetrode of claim 1, wherein the electrodes comprise four electrodes arranged in a square array shape.

5. The tetrode of claim 1, wherein at least one of the electrodes apply electrical stimulation to the living body.

6. The tetrode of claim 1, further comprising a channel located between the electrodes being separate from the electrodes,
   wherein a fluid flows in the channel.

7. The tetrode of claim 6, further comprising a light waveguide arranged in the channel.

8. The tetrode of claim 7, further comprising a reflective layer surrounding the light waveguide.

9. The tetrode of claim 1, wherein the insulation layer contains a biocompatible polymer.

10. The tetrode of claim 1, wherein the insulation layer contains a flexible polymer.

11. The tetrode of claim 1, wherein the insulation layer contains polyimide or polydimethylsiloxane (PDMS).

12. The tetrode of claim 1, wherein the electrodes contain conductive materials.

13. The tetrode of claim 1, wherein a plurality of tetrodes for measuring bio-signals are arranged in a 2D array.

* * * * *